United States Patent [19]

Kalra

[11] Patent Number: 4,701,441
[45] Date of Patent: Oct. 20, 1987

[54] METHODS AND COMPOSITIONS FOR STIMULATION OF APPETITE

[75] Inventor: Satya P. Kalra, Gainesville, Fla.

[73] Assignee: University of Florida, Gainesville, Fla.

[21] Appl. No.: 700,870

[22] Filed: Feb. 11, 1985

[51] Int. Cl.$^4$ .................. A61K 35/39; A61K 37/24
[52] U.S. Cl. .................................... 514/12; 514/21; 424/110
[58] Field of Search ............... 514/12, 21; 424/110

[56] References Cited

U.S. PATENT DOCUMENTS

| | | | |
|---|---|---|---|
| 3,842,063 | 10/1974 | Chance | 424/110 |
| 4,175,122 | 11/1979 | Lazarus | 514/21 |
| 4,223,017 | 9/1980 | Lazarus | 514/21 |
| 4,355,025 | 10/1982 | Lazarus | 514/21 |
| 4,438,104 | 3/1984 | Kimball et al. | 514/2 |

FOREIGN PATENT DOCUMENTS 1373310  11/1974  United Kingdom .

OTHER PUBLICATIONS

Qu et al., "Effect of Intracerebroventricular . . ." Shengli Xuebao 1984 36(4), 331–5, cited in Chem. Abstracts, vol. 102:896w 1985.
Gray et al. cited in Chem. Abstracts, vol. 97:193390n 1982.
Morley et al., cited in Chem. Abstracts, vol. 101:222923w 1984.
Stanley et al., *Life Sciences*, vol. 35, pp. 2635–2642 (1984).
Tatemoto, *Proc. Natl. Acad. Sci.*, vol 79, pp. 5485–5489 (1982).
Tatemoto, *Nature*, vol. 296, Apr. 15, 1982.
Clark et al., *Endocrinology*, vol. 115, No. 1 (1984).
Levine, *Peptides*, vol. 5, pp. 1025–1029 (1984).
Brown et al., *Can J. Physiol. Pharmacol.*, vol. 61, pp. 282–289 (1983).
Blundell, in Eating and its Disorders, Stunkard and Stellar, eds. Raven Press, N.Y. (1984).
Zipf et al., *J. Clin Endocrin. Metab.*, vol. 52, No. 5 (1981).
Konturek et al., *Peptide*, vol. 2, Suppl. 2, pp. 235–241 (1981).
Coy et al. *J. Physiol.*, vol. 314, pp. 225–235 (1981).
Malaisse et al., Chem. Abstract, vol. 87:99656z, 1977.

*Primary Examiner*—Johnnie R. Brown
*Assistant Examiner*—Jacqueline M. Stone
*Attorney, Agent, or Firm*—Dennis P. Clarke

[57] ABSTRACT

A method for the stimulation of the appetite of human and non-human animals comprising administration to the brain of the animal a polypeptide designated Pancreatic Hormone III or a pharmaceutically acceptable salt or metal complex thereof.

10 Claims, 3 Drawing Figures

METHODS AND COMPOSITIONS FOR STIMULATION OF APPETITE

BACKGROUND OF THE INVENTION

1. Field of the Invention

The present invention relates to compositions and methods for the stimulation of appetite in human and non-human animals.

2. Prior Art

The precise biochemical mechanisms inherent in appetite, hunger, satiety, anorexia nervosa, etc., have eluded researchers for years. New avenues of research have led to new insights on the nature of these conditions and have suggested new compositions and methods for the control of appetite.

For example, Malaisse et al [Experientia, 33(7), pp. 915-17 (1977)] identified a pancreatic polypeptide (PP) and found that the administration of bovine PP reduced food intake and suppressed body weight gain in hyperphagic obese mice.

Coy et al [J. Physiol, 314, pp. 225-235 (1981)] discuss the appetite suppressing properties of a peptide, pyro-Glu-His-Gly-OH derived from the urine of patients with hypothalamic anorexia nervosa. The peptide is designated anorexigenic peptide (AP).

Konturek et al [Peptides, 2 (21, pp. 235-240 (1981)] conducted research on the effect of thyrotropin releasing hormone (TRH), a tripeptide (p-Glu-His-Pro-$NH_2$), and AP on gastrointestinal secretions and further demonstrated that the intravenous administration of TRH suppressed food intake.

Zipf et al [J. Clin. Endocrin. Metab., 52 (6), pp. 1264-1266] suggest that pancreatic polypeptide (PP) may be useful to suppress appetite and demonstrated that intravenous administration of bovine PP in obese mice resulted in a decrease of food intake and a decrease in weight gain.

Brown et al [Can. J. Physiol. Pharmacol., 61, pp. 282-289 (1983)] discuss the role of various gastrointestinal peptides in appetite and food intake control.

Lazarus [U.S. Pat. No. 4,355,025] discloses that pancreatic polypeptides derived from vertebrates (VPP), designated "pancreatic hormone III", are useful in the control of appetite and food intake in obese patients.

Conversely, a variety of agents have been suggested for the stimulation of appetite and an increase in the food intake of vertebrates, e.g., herphagic urine (a peptide fraction extracted from the urine of anorexia nervosa patients), chloralore, meprobamate, barbiturates, benzodiazepines, the neuroleptics (chlorpromazine, promazine, clozapine), 5-HT antagonists (cyproheptadine, methylsergide, WA 335-BS, opiate agonists, clonidine, yohimbine, insulin, 2-deoxy-d-glucose, 5-thioglucose, androgens, formamidines, caffeine and opioid peptides. See Blundell, "Systems and Interations; An Approach to Pharmacoloty of Eating and Hunger", Eating and Its Disorders, Ed. Stunkard et al, pp. 39-65, Raven Press, NY (1984) and Morley et al, Neurosci. Biobehav. Rev., Vol. 7, pp. 281-305 (1983) for a discussion of the effect of conventional appetite stimulants on animals.

SUMMARY OF THE INVENTION

The foregoing and other objects are realized by the present invention which provides novel compositions and methods for the stimulation of appetite in human and non-human vertebrate animals based on the discovery that the direct administration to the brain of VPP (a vertebrate pancreatic polypeptide designated Pancreatic Hormone III) or NPY (neuropeptide Y) or pharmaceutically acceptable derivatives, analogs, salts or complexes thereof stimulates the appetite of the human or animal.

More specifically, the invention provides a method for the stimulation of appetite in human or non-human vertebrate animal in need of appetite stimulation and body weight gain comprising administering to the brain of said animals an effective appetite stimulating amount of a polypeptide designated neuropeptide Y or Pancreatic Hormone III or a pharmaceutically acceptable derivative, analog, salt or complex thereof.

The invention also provides a pharmaceutical composition in unit dosage form adapted for administration to the brain of an animal in need of appetite stimulation and body weight gain comprising an effective appetite stimulating amount of a polypeptide designated neuropeptide Y or Pancreatic Hormone III or a pharmaceutically acceptable derivative, analog, salt or complex thereof and a pharmaceutically acceptable carrier therefor.

DETAILED DESCRIPTION OF THE INVENTION

Figure 1:
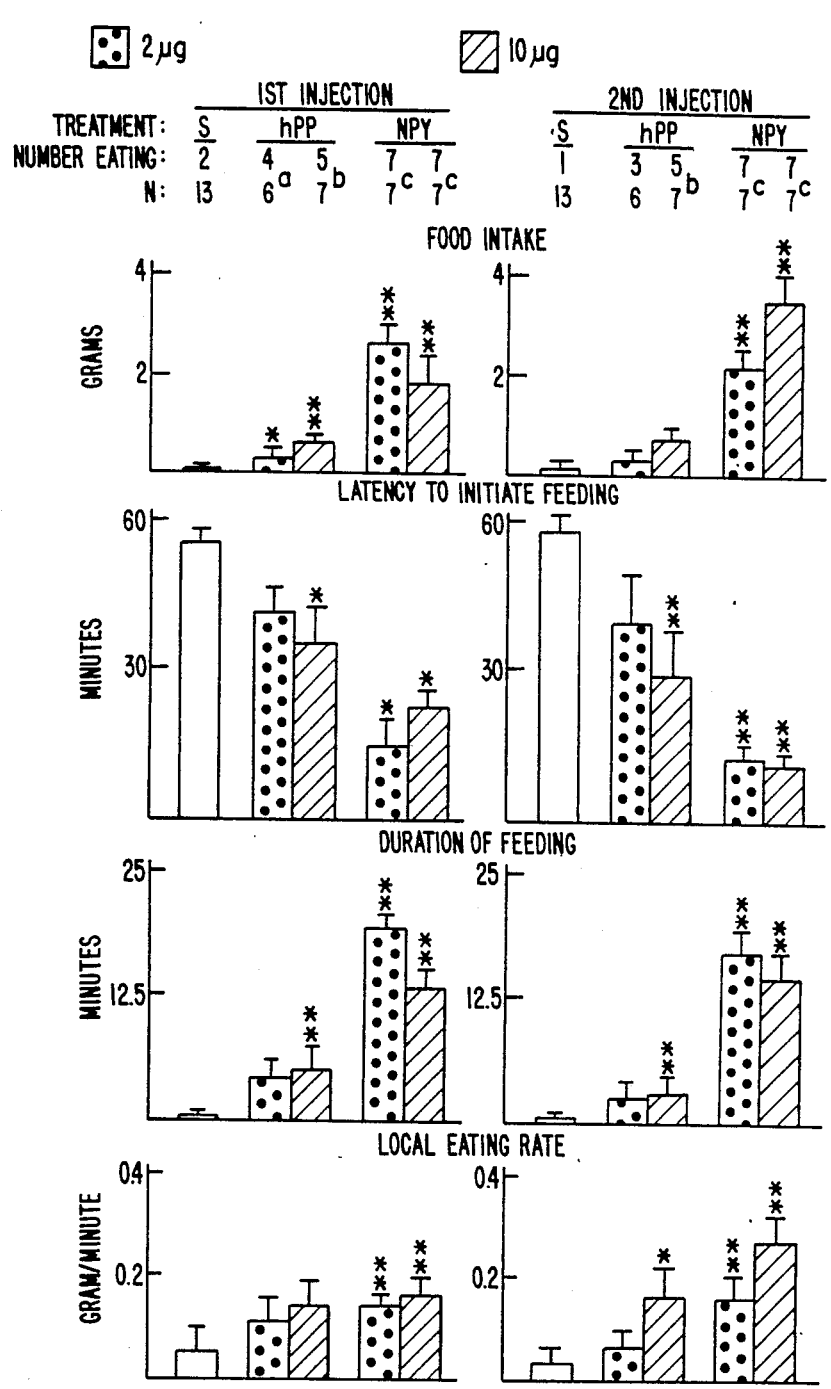

The discovery that VPP or Pancreatic Hormone III and NPY, which has structural similarities to VPP, actually stimulate appetite in animals when administered directly to the brain of animals is most surprising in view of the fact that all of the available research data collected to date [Cf. references discussed above] indicate that the administration of vertebrate pancreatic peptides and peptides analogous thereto to animals in routes other than by direct injection into the brain has precisely the opposite effect, namely, the suppression of appetite and diminishment of food intake.

Without intending to be bound by any theory, the following is offered as a hypothesis of the mechanisms underlying the appetite stimulating effects of the compositions and methods of the invention.

As noted above, accumulating evidence indicates that a number of gastrointestinal, pancreatic and brain hormones may function as modulators of feeding behavior [Schneider et al (1983), Brain Peptides, Wiley Interscience, New York, p. 251; Morley et al (1973), Neurosci. Biobehav. Revs. 7: 281]. Recently, Tatemoto, Proc. Natl. Acad. Sci. USA. 79; 5485 (1982) reported the amino acid sequence for neuropeptide Y (NPY) isolated from porcine brain. NPY displayed considerable structural homologies with a number of pancreatic polypeptides including human pancreatic polypeptide (hPP) [Tatemoto, supra; Tatemoto et al (1982), Nature 296:659]. The detailed distribution pattern of neurons displaying NPY-like immunoreactivity in the rat brain has been described [Allen et al (1983), Science 221:877; Allen et al (1983), 13th Ann. Mtg. Soc. Neurosci. 9:291 (Abstr.); O'Donohue et al (1983), 13th Ann. Mtg. Soc. Neurosci. 9:290 (Abstr.)]. The physiological significance of NPY-like immunoreactivity in the rat brain is presently unknown. During the course of characterizing the effects on LH release in estradiol benzoate-progesterone-treated ovariectomized rats, it was noticed that after intraventricular (ivt) administration of hPP, rats displayed enhanced ingestive behavior.

There is a high degree of amino acid sequence homology between NPY and hPP, as well as between NPY and other members of the pancreatic polypeptide family [Tatemoto, supra; Tatemoto et al, supra; Allen, Y. S., et al, supra]. It would seem that NPY [Allen, Y. S. et al, supra; Allen, Guy J. et al, supra] or NPY-like peptide [Tatemoto et al, supra; O'Donohue et al, supra] which is abundant in the rat and porcine brain, or a specific sequence within NPY, may be the neurotransmitter or neuromodulator which normally plays a role in regulating feeding behavior in these species. Further, NPY-like immunoreactivity has been observed in many cortical, hypothalamic and limbic regions [Allen, Y. S. et al, supra; Allen, Guy J. et al, supra; O'Donohue et al, supra], some of which may mediate ingestive behavior [Schneider et al, supra; Morley et al, supra; and Leibowitz (1975), Physiol. Behav. 14:731]. Presumably, after ivt injections, NPY and hPP reached receptive elements (in the vicinity of the cannula sites or elsewhere in the brain) on components of the neuronal circuitry involved in elicitation of the feeding response [Schneider et al, supra; Morley et al, supra] and Van Der Gugten et al (1977), Pharmacol. Biochem. Behav. 7:211]. It is also possible that NPY or hPP may release endogenous opioid peptides [Morley et al, supra] or catecholamines (norepinephrine, epinephrine) [Leibowitz, supra; and Van Der Gugten et al, supra] in crucial brain sites, which may in turn activate feeding in the rats.

It is to be understood that by the generic term vertebrate pancreatic polypeptide (VPP) or the specific pancreatic polypeptides (PP) derived from bovine (BPP), porcine (PPP), avians (APP), humans (HPP), ovine (OPP), rodent (rat) (RPP), etc., is meant the peptide(s) isolatable by the method described in Endocrinology, 83 1323 (1968) and 93, 558 (1973) and by Kimmel et al, J. Biol. Chem., 250 (24), 9369 (1975). The amino acid sequences of the various PP's are set out in Gastroenterology, 47(4), 737 (1974) and Kimmel et al, Endocrinology, 114(5), 1725 (1984). The polypeptides are identified as straight-chain sequences of thirty-six amino acid residues having identities at fifteen positions. For example, PPP, OPP and HPP differ from BPP in only one or two residues at positions 2, 6 or 23.

Kimmel et al, supra, suggestd that the name "Pancreatic Hormone III" (PH-III) be used to generically designate the vertebrate pancreatic polypeptides (VPP) referred to herein. Kimmel assigns to BPP and APP the following structures:

BPP-Ala.Pro.Leu.Glu.Pro.Gin.Tyr.Pro.Gly.Asp.Asp-.Ala. Thr.Pro.Glu.Gin.Met.Ala.Gin.Tyr.Ala.Ala.-Glu.Leu. Arg.Arg.Tyr.Ile.Asn.Met.Leu.Thr.Arg.-Pro.Arg.TyrNH$_2$

APP—Gly.Pro.Ser.Gin.Pro.Thr.Tyr.Pro.Gly.Asp.Asp.Ala.
 1    6    12

Pro.Val.Glu.Asp.Leu.Ile.Arg.Phe.Tyr.Asp.Asn.Leu.
 13    18    24

Gin.Gin.Tyr.Leu.Asn.Val.Val.Thr.Arg.His.Arg.TyrNH$_2$
 25    30    36.

Published United Kingdom Patent Specification No. 1,373,310, U.S. Pat. No. 3,842,063 and Swiss Pat. No. 551,949 teach inter alia structures for VPP's (Pancreatic Hormone III) of respectively bovine, porcine, ovine and human origin, together with the extraction and isolation of the polypeptides from pancreas and their characterization. VPP's of known structure may be synthesized by classical peptide synthetic methods and VPP's of other species may be isolated from pancreas by procedures analogous to those taught in the references mentioned herein. Such procedures are themselves analogous to classical extraction procedures used for the separation of insulin and typically include an initial acid/alcohol extraction of the pancreatic material, removal of lipic, concentration, and fractional separation of the insulin, glucagon and VPP (Pancreatic Hormone III) by one or more of a variety of methods including gel filtration, ion exchange chromatography, electrophoresis and countercurrent distribution.

The isolation and structure of porcine neuropeptide (NPY) was reported by Tatemoto, supra and Tatemoto et al, supra. Analogous NPY peptides can be derived by similar methods from the brains of sheep, oxen, birds and humans. Tatemoto assigned the following structure to NPY:

Tyr. Pro. Ser. Lys. Pro. Asp. Asn. Pro. GLy. Glu. Asp. Ala. Pro. Ala. GLu. Asp. Leu. Ala. Arg. Tyr. Tyr. Ser. Ala. Leu. Arg. His. Tyr. Ile. Asn. Leu. Ile. Thr. Arg. GLn. Arg. Tyr. NH$_2$

NPY resembles porcine PP in 18 of its 36 residues as underlined. It shows identical residues of 17; with bovine PP and of 20 residues with avian PP.

The VPP's and NPY's may be administered to the brain according to any conventional technique, e.g., intracerebroventricularly, to stimulate the appetite of any human or non-human vertebrate animal suffering from anorexia nervosa, loss of appetite due to general fever, illness due to damage or lesion of the brain region controlling "appetite", or due to brain tumor resulting in decreased appetite and in vertebrate animals for fattening and growth as desired by meat and poultry industry.

The VPP's and NPY's may be administered in admixture with any suitable pharmaceutically acceptable carrier or, optionally, other therapeutic ingredients as a composition particulary adapted for administration directly to the brain of a human or non-human vertebrate animal. The compositions are prepared in unit dosage form according to any of the methods known in the art of pharmacy.

Each unit dosage should contain from about 2 $\mu$g to about 100 mg, preferably from 2 $\mu$g to about 1 mg of peptide.

The amount of peptide required to effectively stimulate the appetite of an animal will obviously vary depending upon such variable parameters as the identity of the animal and the peptide and the nature and severity of the condition treated. Generally, however, a suitable does of peptide may vary from about 1 $\mu$g to about 100 mg/kg of animal body weight, preferably from about 1 $\mu$g to about 10 mg/kg.

It will be understood that the pure peptide may be administered to the animal or any pharmaceutically acceptable salt, analog, derivative or complex thereof. Suitable such salts, complexes and derivatives are identified in U.S. Pat. No. 4,355,025.

It is preferred that the peptide be derived from the same species of animal as that to which it is administered in order to avoid any inter-species complications.

The invention is illustrated by the following non-limiting examples.

EXAMPLE 1

Adult female rats (CRL:CD®(SD)BR, Charles River Breeding Labs, Wilmington, MA) were maintained in individual wire bottom cages under controlled temperature and light (lights on 0500–1900 h) with ad libitum access to food and water. Rats were ovariectomized and permanent cannulae were implanted in the third cerebral ventricle under pentobarbital anesthesia (40 mg/kg, 9). Eleven to 13 days after surgery, rats were treated with estradiol benzoate (30 μg in 0.1 ml sesame oil, sc) and progesterone (15 mg in 0.3 ml sesame oil, sc). Two days later (0900-0900 h), food and water were removed and patency of the ivt cannula was checked by observing efflux of cerebrospinal fluid. Two hours later, the effects on food intake of two ivt injections, 65 min apart, of saline (3 μl), hPP (2 or 10 μg is saline, Boehringer Mannheim, Indianapolis, IN), or porcine NPY (2 or 10 μg in saline, Peninsula Laboratories, Belmont, CA) were assessed. Immediately after the ivt injections, rats were returned to their home cages which contained a known amount of rat chow and observed for 60 min. The behavior was recorded in 5 mutually exclusive categories: eating, grooming, locomotion, resting and other [Blundell, Bio-grammar of Feeding: Pharmacological Manipulations and Their Interpretations. In: Cooper, S. J. (ed) Theory in Psychopharmacology, Academic Press, N.Y., Vol. I: 233 (1981)] the following measurements were derived; total food intake (g); latency to feeding response (min); duration of time spent eating (min); number of eating bouts (n); duration of eating bouts (min) and local eating rate (g/min). Local eating rate is a measure of amount of food consumed per unit time spent eating.

After the second ivt injection of saline or peptide, rats also had access to water. Although no attempt was made to quantify the water intake, the latency to drinking and amount of time spent on drinking were monitored.

The effects of hPP and NPY on food intake were evaluated in 2 experiments, each with its own control. Since there were no differences in the control groups for Experiments 1 and 2, the data were combined for statistical analyses. The number of animals feeding and drinking after peptide treatment were compared with saline-treated rats by the Fisher exact probability test. Parameters of ingestive behavior of controls vs. peptide treated groups were analyzed by the Mann-Whitney U test. Comparisons within groups of parameters after the first and second injections were made with the Wilcoxon matched pairs - signed rank test.

The results are shown in FIG. 1 which depicts the effects of ivt administration of hPP or NPY on parameters of feeding behavior in ovariectomized rats pretreated with estradiol benzoate plus progesterone wherein values are mean ±SE. (*=P<0.05; **=P<0.01, Mann-Whitney U tests; a=p<0.05; b=P<0.025; c=P<0.005, Fisher Exact Probability Test) and S=saline.

Figure 2:
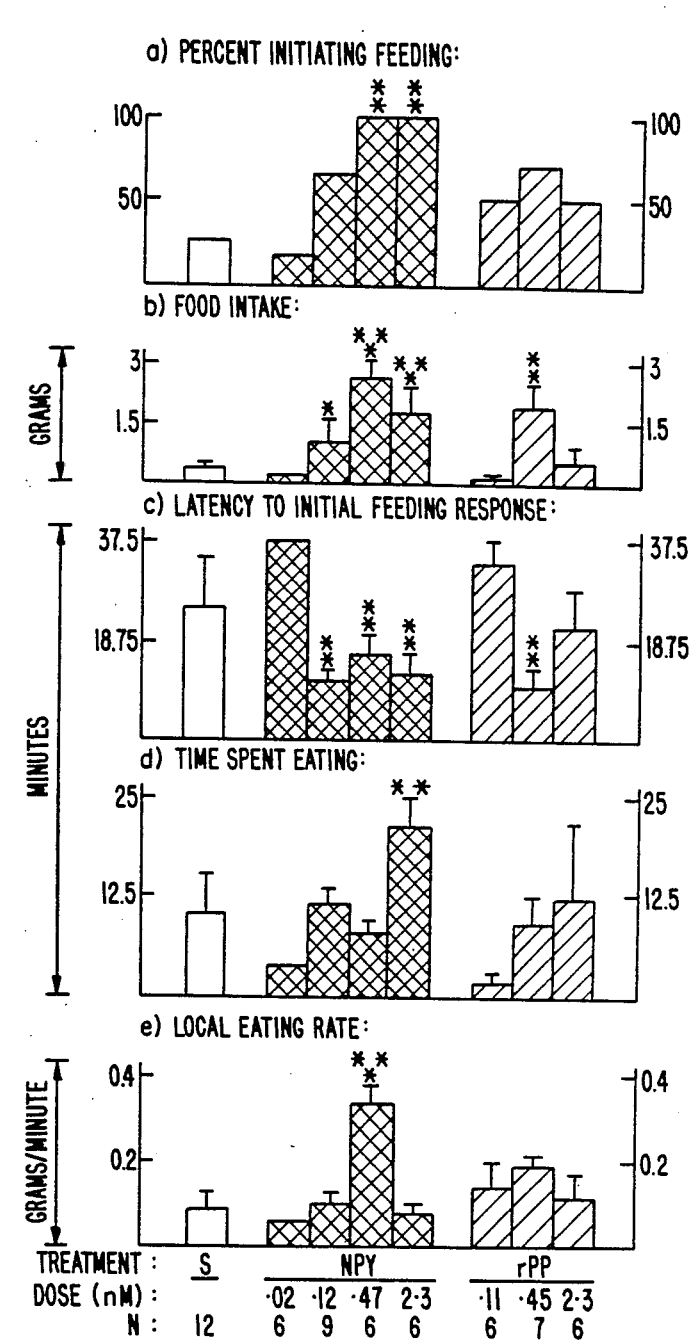

It is apparent from FIG. 1, 2 or 10 μg of hPP or NPY stimulated cumulative food intake as compared with saline treated control rats. Furthermore, NPY was more effective than hPP in eliciting several aspects of ingestive behavior. Whereas NPY elicited feeding in all treated rats after the first injection, only 4/6 rats treated with 2 μg hPP and 5/7 rats treated with 10 μg hPP ate. Additionally, NPY treated rats ate 3-fold higher amounts and spent more time on eating after each injection. Importantly, NPY elicited the first feeding response with a shorter latency than hPP (P<0.02). It is noteworthy that after the first 2 or 10 μg NPY injection there was a similar cumulative food intake, but a dose-related food intake was found after the second injection, which can be attributed to a similar dose-dependent increment seen in local eating rate concomitant with unchanged time spent on feeding.

There were significant differences in the effects of the two peptides on grooming and drinking behavior. Neither peptide altered the number of rats grooming during the observation periods, but NPY-treated rats spent less time grooming than did saline or hPP-treated animals (P<0.05). Furthermore, whereas 2 or 10 μg NPY significantly increased the number of animals drinking and the amount of time spent drinking (P<0.02) only the higher does of hPP produced a similar response (P<0.02). Finally in 3/7 rats treated with 10 μg hPP, 5/7 treated with 2 μg NPY and 6/7 treated with 10 μg NPY, the drinking response preceded the feeding response.

The tests were also conducted on intact cycling and ovariectomized rats, where NPY was found to be equally effective in stimulating the feeding response.

EXAMPLE 2

The procedure of Example 1 was repeated utilizing intact male and female rats and porcine NPY.

The results are set forth in table 1 (n=number of rats).

TABLE 1

|  | Cumulative food intake (g/h) |
|---|---|
| Intact females | |
| Saline (n = 5) | 0.08 (515) |
| NPY (2 μg, n = 6) | 2.34 ± 0.28 (616) |
| Intact males | |
| Saline (n = 6) | 0.47 ± 0.13 (316) |
| NPY (2 μg, n = 6) | 2.64 ± 0.46 (616) |

The above procedure was repeated except that 2 and 10 μg of NPY were administered intravenously to an equal number of male rats. The results indicate a failure of the intravenously administered NPY to stimulate food intake.

EXAMPLE 3

Figure 3:
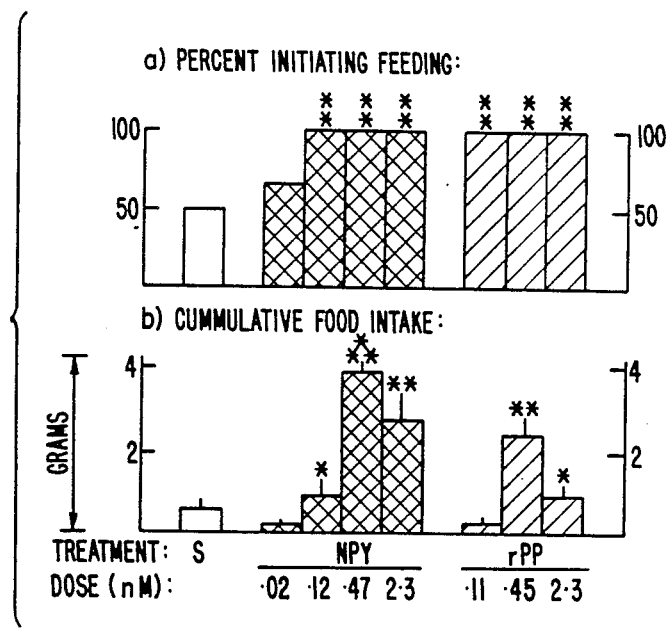

NPY and rat pancreatic polypeptide (RPP) were administered to normal adult male rats according to the procedure of Example 1. The parameters of the procedure and the results are set forth in FIG. 2, wherein in (a), **=p<0.025, Fisher Exact Probability test compared to saline treated rats; in (b), *=p<0.05, *=p<0.01, Mann Whitney U-test; in (c), =p<0.025, Mann Whitney U-test in (d), *=p<0.01, Mann Whitney U-test; in (e), *=p<0.01, Mann Whitney U-test, and in FIG. 3 wherein in (a), **=p<0.025, Fisher Exact Probability test and in (b), *=p<0.05, =p<0.02 and *=p<0.01, Mann Whitney U-test.

These results indicate an enhanced cumulative food intake which is dose-dependent on the administration of NPY and RPP.

I claim:
1. A method for the stimulation of appetite in human or non-human, vertebrate animals in need of appetite stimulation or body weight gain comprising directly administering to the brain of said animal an effective appetite stimulating amount of a polypeptide designated Pancreatic Hormone III compatible with the species of said animal to which it is administered or a pharmaceutically acceptable salt or metal complex thereof.

2. The method of claim 1 wherein said Pancreatic Hormone III is human-derived and is administered to a human.

3. The method of claim 1 wherein said Pancreatic Hormone III is porcine-derived and is administered to a porcine mammal.

4. The method of claim 1 wherein said Pancreatic Hormone III is bovine-derived and is administered to a bovine mammal.

5. The method of claim 1 wherein said Pancreatic Hormone III is ovine-derived and is administered to an ovine mammal.

6. The method of claim 1 wherein said Pancreatic Hormone III is avian-derived and is administered to a bird.

7. The method of claim 1 wherein said Pancreatic Hormone III is rodent-derived and is administered to a rodent.

8. The method of claim 1 wherein said Pancreatic Hormone III or pharmaceutically acceptable salt or metal complex thereof is administered in an amount of from 1 μg to 100 mg per kg body weight of the animal treated.

9. The method of claim 1 wherein said Pancreatic Hormone III is administered intracerebroventricularly.

10. The method of claim 1 wherein said Pancreatic Hormone III or salt or metal complex thereof is administered to said animal to increase the weight thereof.

* * * * *

UNITED STATES PATENT AND TRADEMARK OFFICE
CERTIFICATE OF CORRECTION

PATENT NO. : 4,701,441
DATED : October 20, 1987
INVENTOR(S) : Satya P. KALRA It is certified that error appears in the above-identified patent and that said Letters Patent is hereby corrected as shown below:

Column 1, line 6, after "BACKGROUND OF THE INVENTION" and before "Field of the Invention", insert the following paragraph:

--This invention was made with Government support under Grant HD-08634 awarded by the National Institutes of Health. The Government has certain rights in the invention.--

Signed and Sealed this

Sixteenth Day of March, 1993

*Attest:*

STEPHEN G. KUNIN

*Attesting Officer*     *Acting Commissioner of Patents and Trademarks*